United States Patent [19]
Terasaki et al.

[11] Patent Number: 4,797,475

[45] Date of Patent: Jan. 10, 1989

[54] METHOD AND COMPOSITION FOR ISOLATING WHITE CELL ELEMENTS

[75] Inventors: Paul I. Terasaki, Los Angeles; Jimmy Loon, Reseda; Steven Hardiwidjaja, Simi Valley; Nadim El-Awar, Burbank, all of Calif.

[73] Assignee: The Regents of the University of California, Berkeley, Calif.

[21] Appl. No.: 756,393

[22] Filed: Jul. 17, 1985

Related U.S. Application Data

[63] Continuation of Ser. No. 496,638, May 20, 1983, abandoned.

[51] Int. Cl.$^4$ .................. G01N 33/48; G01N 1/18; G01N 33/559; G01N 33/53
[52] U.S. Cl. ..................... 530/387; 424/85.8; 424/101; 514/2; 435/240.1; 435/240.2; 435/240.21; 436/63; 436/171; 436/514; 436/518; 436/821; 436/824
[58] Field of Search ............... 435/240, 241, 259, 261, 435/803, 240.2, 240.21, 240.1; 530/381, 387; 424/11, 85, 101; 436/519, 548, 821, 824, 63, 177

[56] References Cited

U.S. PATENT DOCUMENTS

| | | | |
|---|---|---|---|
| 4,192,917 | 3/1980 | Zurawski, Jr. ................. | 435/236 |
| 4,361,549 | 11/1982 | Kung et al. ..................... | 424/85 |
| 4,361,550 | 11/1982 | Kung ............................ | 424/85 |

OTHER PUBLICATIONS

Grumet et al. *Human Immunology* vol. 6 pp. 63–73 1983 "A Simplified New Method for HLA-DR Typing Using the TMI Monoclonal antibody".

Mishell et al. *Selected Methols in Cellular Immunology* pp. 211–212 1980.

Morgan et al. *Blood* vol. 18 1961 pp. 89–94 "Separation of Platlets from Whole Blood by the Use of Silicone Fluids".

Pollack et al. *Clin Immunol Immunopathol* vol. 25(1) 1982 pp. 15–25 "The Functional Study of DR Positive Human Epidermal Langerhans Cells . . . ".

Lundak et al. *J. Immunol Methods* vol. 28(3–4) 1979 pp. 277–242 "Separation of Functional Subpopulations of Minke and Lymphoid cell . . . ".

Biological Abstracts, vol. 68, No. 7, 1979, p. 4138, abstract No. 41418, Philadelphia, PA, US; J. W. Chiad et al.: "Isolation of Human T Lymphocytes by a Negative Selection Procedure", & Immunol. Commun. 8(1): 49–54, 1979 * Abstract *.

Tissue Antigens, vol. 16, 1980, pp. 317–325, Munksgaard, Copenhagen, DK; T. A. De Kretser et al.: "The Separation of Cell Populations Using Monoclonal Antibodies Attached to Sepharose" p. 317, Abstract; p. 324, Last Paragraph of "Discussion"*.

Biological Abstracts, vol. 61, 1st Feb. 1976, p. 1491, Abstract No. 14367, Philadelphia, PA, US; V. Ghetie et al.: "Cell Separation by Staphylococcal Protein A—Coated Erythrocytes" & Scand. J. Immunol. 4(5/6): 471:477, 1975 * Abstract *.

Chemical Abstracts, vol. 69, No. 9, 26th Aug. 1968, p. 3120, Abstract No. 33491p, Columbus, Ohio, US; H. Pertoft et al.: "Separation of Various Blood Cells in Colloidal Stlicapoly(vinyl–pyrrolidinone) Gradients", & EXP. Cell Res. 1968, 50(2), 355–368 * Abstract *.

Primary Examiner—Thomas G. Wiseman
Assistant Examiner—Robin L. Teskin
Attorney, Agent, or Firm—Poms, Smith, Lande & Rose

[57] ABSTRACT

A composition of matter and method for using the composition of matter to isolate various cell elements from a heterogeneous cell suspension in a simple one step procedure. The composition is a monoclonal antibody mixture including complement and a non-toxic density gradient media. The composition provides a negative selection technique in which undesired subpopulation cells are lysed and separated from the desired cell subpopulation. The invention has particular application to isolation of white cell elements.

18 Claims, No Drawings

METHOD AND COMPOSITION FOR ISOLATING WHITE CELL ELEMENTS

This is a continuation of application Ser. No. 496,638 filed May 20, 1983 abandoned.

BACKGROUND OF THE INVENTION

The present invention relates generally to a method and composition for separating subpopulations of cells from heterogeneous cell suspensions. More particularly, the present invention relates to separation and isolation of lymphocytes and accessory cells.

The suspended particles of blood comprise approximately 45 percent of the total volume of blood. The suspended particles include red blood cells (erythrocytes), white blood cells (leukocytes) and platelets (thrombocytes). Although the great majority of the cells in blood are red blood cells, the white blood cells are extremely important since they are the body's primary defense against infections.

There are basically three types of white blood cells: the lymphocytes, the granulocytes and the monocytes. The lymphocytes are further classified as T lymphocytes, B lymphocytes and Null lymphocytes. The T-lymphocytes may be further classified into subpopulations identified a helper T-lymphocytes and suppressor T-lymphocytes. The granulocytes are also further classified as neutrophils, eosinophils and basophils. The white blood cells are also classified generally as lymphocytes and accessory cells. The lymphocytes include the T, B ad Null lymphocytes. The granulocytes and monocytes are classified as accessory cells.

Past progress in understanding the cellular immunology of the white blood cells and future progress in further understanding of the white blood cells is dependent upon our ability to separate and isolate the various lymphocytes and accessory cells to allow their identification and analysis. Due to the importance of separating and distinguishing white blood cells subpopulations, a wide variety of cell separation procedures have been developed. Common techniques presently employed for separating and isolating white blood cell populations include adherence type processes in which one or more of the white blood cell types are removed by adherence to various materials such as Sephadex and nylon wool. Other procedures have utilized density gradients to separate the white blood cell populations into their respective classes by size and density differences.

In order for a cell separation method to be useful, the separation technique must be simple and produce high, representative yields of the desired cells with little or no contamination by other white blood cell types. The separation technique should also be easily reproducible and not adversely affect the behavior of the recovered white cell population. Although the above mentioned cell separation methods are fairly successful, these methods still require a considerable number of steps which are not only time consuming but increase the chance for sample mix-up.

Recently, a new cell isolation and separation method has been developed which is based upon the specific cell surface markers present in each of the white blood cell types. Basically, the method involves treating the heterogenous population of white blood cells (which generally will also include some red blood cells) with one or more specific antibodies which recognize and become attached to one or more of the white cell subpopulations. Complement is then added to the cells to lyse the antibody tagged cells. The lysed cells are then separated from the remaining non-lysed heterogeneous white cell population. This negative selection type method has shown some promise; however, disadvantages have included suitable sources of antisera and complement which provide the desired lysing of the white cell subpopulation that is to be removed from the heterogeneous white cell population. Also, separate steps involving antibody treatment, complement lysing of cells and separation of the lysed cells from the desired cell subpopulation are required.

In view of the importance of optimum separation and isolation of the various white cell elements, it is desirable to provide isolation methods and reagents useful in such methods which simplify cell isolation procedures, enhance cell separation and provide optimum yields of desired viable cells.

SUMMARY OF THE INVENTION

In accordance with the present invention, a new composition of matter and method for using the composition is provided for isolating various cell elements from a heterogeneous cell suspension in a simple one step procedure. The present invention is based on the discovery that monoclonal antibodies may be combined together with complement and non-toxic density gradient media to provide a composition of matter which is useful in separating a subpopulation of cells bearing specific markers from a heterogeneous cell suspension. The composition of matter is referred to hereinafter as either a monoclonal antibody mix or monoclonal antibody cocktail.

The monoclonal antibody mix basically includes one or more monoclonal antibodies which specifically recognizes or is immunoreactive with a specific immunogenic marker or antigen on the subpopulation of cells which is to be removed from the heterogeneous cell suspension. As is well known, monoclonal antibodies to a given cell are capable of immunoreacting with specific markers on the cell to form an antibody tagged or labeled subpopulation of cells. The monoclonal antibody mix further includes complement in an amount sufficient to provide lysing of the antibody tagged subpopulation cells to produce a subpopulation of lysed cells which have a density typically less than the non-lysed cells in the heterogeneous cell suspension. The monoclonal antibody mix further includes a sufficient amount of a non-toxic density gradient media to provide an aqueous solution which has a density greater than the lysed subpopulation cells, but less than the density of the remaining non-lysed cells.

The method for using the monoclonal antibody mix to separate a subpopulation of cells having specific markers from a heterogeneous cell suspension basically involves mixing the heterogeneous cell suspension with the monoclonal antibody mix for a sufficient time and at a sufficient temperature to form a lysed subpopulation of cells and non-lysed cells. The monoclonal antibody mix with lysed subpopulation cells and non-lysed cells is then centrifuged by conventional means. During centrifugation the lysed cells move to the surface for subsequent removal while the non-lysed cells move to the bottom of the gradient. Centrifugation of the lysed and non-lysed cells in the density gradient media present in the monoclonal antibody mix provides a convenient means for separation of the cells.

The present invention is an improvement over prior art techniques in which antibody tagging, complement induced lysing and final separation of non-lysed cells from lysed cells is carried out in two or more separate steps. The present invention allows cell isolation or separation to be carried out in a single step and in a single test tube to thereby avoid the possibility of sample mix-up which is present any time the sample must be transferred from one tube to another while working with multiple samples.

The present invention has particular application to separating and isolating various white blood cell subpopulations from a heterogeneous white blood cell suspension. The monoclonal antibody mix has been found to markedly simplify lymphocyte isolation procedures and to reduce the time previously required in procedures where more than one cell treatment step is required.

Although it might have been suspected that the monoclonal antibodies or complement or density gradient media when mixed together might interfere with each other or adversely affect the subsequent reactivity of lymphocytes or accessory cells, we have found no detectable difference in the reactivity of lymphocytes isolated by our present invention and those isolated by standard methods.

The above discussed and many other features and attendant advantages of the present invention will become apparent as the invention becomes better understood by reference to the following detailed description.

DETAILED DESCRIPTION OF THE INVENTION

The present invention deals basically with a one step procedure for isolating desired subpopulation of cells from a heterogeneous cell population. The present invention includes not only the procedure for separation and isolation of the cells, but also includes a new composition of matter for use in carrying out cell separation procedure. As previously mentioned, the composition of matter is referred to in the specification as a monoclonal antibody mix or monoclonal antibody cocktail.

The present invention has wide application to separating any number of cells or other matter which include antigenic markers which are immunoreactive with antibodies. The present invention has particular application to the separation and isolation of white cell elements. The following detailed description will be limited to the separation and isolation of white cell elements with it being understood that the present invention is not limited to white cell isolation only.

The monoclonal antibody mix in accordance with the present invention is an aqueous solution of: (1) one or more specific antibodies which recognizes and bind to specific antigenic markers on the cell subpopulation which is to be removed from a heterogeneous cell suspension; (2) complement in an amount sufficient to provide lysing of the subpopulation cells when they are tagged with the specific antibody; and (3) a non-toxic density gradient media which is capable of separating the non-lysed cells which are being isolated from the complement lysed subpopulation cells.

The specific antibody or antibodies which are present in the monoclonal antibody mix will depend upon the particular subpopulation of cells which is to be lysed and separated from the heterogeneous cell population. The preferred heterogeneous cell population in accordance with the present invention is the buffy coat which is produced when whole blood is centrifuged. As is conventionally known, when whole blood is sufficiently centrifuged it separates into a lower red blood cell portion and an upper plasma portion. The lower red blood cell portion and upper plasma portion is separated by a buffy cost. The buffy coat includes white blood cell elements and will typically also include some red blood cells. A preferred heterogeneous cell suspension in accordance with the present invention is a suspension of the buffy coat in a suitable aqueous medium such as Hanks medium or normal phosphate buffered saline (PBS). Both Hanks medium and PBS are common laboratory reagents which are widely available and widely used.

The heterogeneous suspension prepared from the buffy coat will include among other things: B lymphocytes, T lymphocytes, null lymphocytes, monocytes and the three types of granulocytes neutrophils, eosinophils, and basophils.

The particular antibody used in a given antibody mixture will depend upon the particular white cell population to be removed from the buffy coat suspension. For example, to isolate lymphocytes from the buffy coat, the antibody mix will include antibodies against red cells, monocytes and the granulocytes. If B lymphocytes are to be isolated antibodies specific to T lymphocytes would be added to the mixture in addition to the antibodies against red cells, monocytes and granulocytes. Alternatively, if T lymphocytes are to be isolated, antibodies against B lymphocytes would be combined with antibodies against red cells, monocytes and granulocytes.

To isolate helper T-lymphocytes from suppressor T-lymphocytes, antibody to suppressor T-lymphocyte would be added to the above described antibody mixture for separating T-lymphocytes. Alternatively, to isolate suppressor T-lymphocytes from helper T-lymphocytes, antibody to helper T-lymphocytes would be added.

To isolate monocytes, the antibody mixture would include antibodies to red cells, lymphocytes and granulocytes. To isolate granulocytes, the antibody mixture would include antibodies against red cells, monocytes and lymphocytes. To isolate a specific type of granulocyte, antibodies directed against the two non-desired granulocytes would be combined with antibodies against red blood cells, lymphocytes and monocytes. For example, to isolate basophils, antibodies against eosinophils, neutrophils, lymphocytes, monocytes and red cells would be necessary in the antibody mix. To isolate eosinophils, antibodies to basophils and neutrophils would be combined with antibodies to lymphocytes, monocytes and red cells in the antibody mixture. To isolate neutrophils, antibodies against eosinophils and basophils would be combined with antibodies against lymphocytes, monocytes and red cells in the antibody mix. The null lymphocytes may be isolated by preparing an antibody mix including antibodies to T and B lymphocytes along with antibodies to monocytes, ganulocytes and red cells.

The antibody to be used in the antibody mix in accordance with the present invention must be specific for the particular white cell element to be removed from the buffy coat cell suspension. Further, the antibody must be sufficiently strong or immunoreactive to provide lysing of the antibody tagged cell when treated with complement. The antibody must also be compatible with complement and the density gradient media.

Although any antibody fitting these criteria may be used, it is particularly preferred that monoclonal antibodies be used as the specific antibodies in accordance with the present invention.

Monoclonal antibodies are well known and widely used. Preparation and use of monoclonal antibodies is conventional. The preparation and isolation of suitable monoclonal antibodies which are specific for the various white cell elements does not form a part of this invention other than the fact that the monoclonal antibody must be isolated and prepared for incorporation into the antibody mix. Conventional techniques for producing monoclonal antibodies which are immunoreactive with specific cell markers are set forth in Kohler G. Milstein Nature 256: 495 (1975), Kohler G. Milstein, European Journal of Immunology, 6: 511 (1976) and S. Fazeks de St. Groth, Journal of Immunological Methods, 35: 1-21 (1980).

As is well known, complement is a complex series of enzymatic proteins occurring in normal serum that intereact to combine with the antigen-antibody complex present on an antibody tagged cell to produce lysing of the cell. Complement is typically isolated from various animals such as rabbits. Complement isolated from any species may be used so long as it does not adversely react with the selected specific monoclonal antibodies in the antibody mix and is capable of providing the desired cell lysing. Also, the complement should not affect the viability or reactivity of the remaining unlysed cell elements and also should be nonreactive towards the density gradient media. Complement isolated from rabbits is preferred.

The density gradient media utilized in accordance with the present invention must have a density greater than the lysed subpopulation cells, but less than the density of the non-lysed cells. Density gradient media such as cesium chloride and colloidal silica gradients are preferred.

Colloidal silica density gradient materials are particularly preferred. Colloidal silica density gradient materials are well known, widely used and available commercially. The colloidal silica density gradient material basically includes colloidal silica particles coated with polymers to stabilize the particles in suspension and make the silica non-toxic to cells. A suitable polymer coating is polyvinyl pyrrolidone (PVP). Colloidal silica coated with PVP is commercially available from Phamacia Corp. under the tradename Percoll. Percoll is a particularly preferred density gradient material since the colloidal silica particles are of different sizes. The different sized particles provide an enhanced separation of lighter lysed cells from the heavier non-lysed cells when the antibody mix is centrifuged. This is believed to be due to the migration of the heavier or larger colloidal silica particles to the bottom of the centrifuge tube to inherently form a density gradient density centrifugation of the antibody mix to provide enhanced separation of lysed cells from non-lysed cells. Density gradient materials which are altered or destroyed during incubation and cell lysing are not suitable.

The three basic antibody mix ingredients (monoclonal antibody or antibodies, rabbit complement and Percoll) are preferably in an isotonic aqueous solution of Hanks medium or PBS.

The actual amount of specific antibody and complement present in the antibody mix will vary depending upon the strength and effectiveness of the antibody and/or complement. The amount of a particular monoclonal antibody or rabbit complement required in the antibody mix or cocktail is determined experimentally. The amount of Percoll in the antibody mix will depend upon the type of cells being isolated and is preferably from between 40 to 60 volume percent of Percoll stock solution wherein the Percoll stock solution is prepared by mixing 9 parts of Percoll commercially supplied from the manufacture with 1 part of 10×PBS (10 times physiological concentration). For isolating lymphocytes, an antibody mixture containing approximately 53 volume percent of the Percoll stock solution is preferred.

An example of practice is as follows:

A monoclonal antibody mixture was prepared for removing red cells and granulocytes from a suspension of buffy coat cells to thereby isolate lymphocytes. Monoclonal antibodies were prepared from ascites produced in Balb/C mice according to the methods of Kohler and Milstein (1978). Spleen cells from immunized Balb/C mice were used with myeloma cells using polyethylene glycol (PEG) and grown in HAT medium to eliminate non-hybridized myeloma cells. The two antibodies produced in this manner were: (1) 70-2B4F7, an anti-red cell antibody in ascites fluid with a titer of 1:2000. This antibody was diluted 1:4 in PBS prior to addition to the antibody cocktail; and (2) 89-4C6A8, an anti-granulocyte in ascites fluid with a titer of $10^{-4}$. This antibody was diluted 1:4 in PBS prior to addition to the antibody cocktail. Rabbit complement (PELFREEZE HLA-A, -B, -C typing) along with Percoll (Pharmacia) density gradient was used. A stock solution of Percoll was prepared by diluting 9 parts of the commercially available Percoll with 1 part 10×phospate buffered saline.

The formulation for the antibody cocktail was as follows:
1. 500 ml rabbit complement.
2. 10 ml of the monoclonal anti-red cell antibody (diluted 1:4).
3. 10 ml of the monoclonal anti-granulocyte antibody (diluted 1:4).
4. 350 ml of the Percoll stock solution The above antibody mixture was used for isolating lymphocytes as set forth in the folowing procedure:
1. Centrifuge 15 cc. whole blood (Heparin or acid citrate dextrose) at 1000 g's for 10 minutes.
2. Draw 0.1 cc (100 microliters) of buffy coat into a Fisher tube containg 1 cc. of normal phosphate buffered saline (PBS) and mix well. Centrifuge in a Fisher centrifuge for 1 minute at 1000 g's.
3. Discard supernatant and resuspend in 0.75 cc. of the monoclonal antibody cocktail and mix well.
4. Incubate mixture in a 37° C. waterbath or heating block for 15 minutes. Cocktail mixture should be a clear, dark red from hemolysis.
5. After incubation, mix well with a pipet to break up any clumps. Layer 0.2 cc of PBS or Hank's medium on top of mixture and centrifuge at 2000 G's for 2 minutes. Remove and discard the resulting floating dead cell layer and supernatant.
6. Wash lymphocyte pellet twice with PBS, Hanks or McCoys medium. Centrifuge cells at 1000 g's for 1 minute after each wash.
7. Resuspend the isolated cells in McCoys medium and adjust concentration to between 1.5 to 2.0 million cells per cc.

Lymphocytes from 43 healthy volunteer donors were isolated using the above described monoclonal antibody cocktail mixture and procedure of the present invention and a separation method described by Terasaki et al. (1978) known as the Ficoll hypaque/thrombin separation technique. The lymphocytes isolated from both procedures were typed in parallel with local HLA-A, -B, -C reagents obtained from multiparous women. The monoclonal antibody method of the present invention required an average of 20 to 25 minutes to complete and yielded up to 5 million lymphocytes with over 90 percent purity. This compared well with the Ficoll-hypaque/thrombin separation technique which takes an average of 30 minutes to complete and yielded up to 3 million lymphocytes from 0.1 cc of buffy coat with a range of 50–90 percent purity.

The results of the parallel testing indicated a discrepancy of only 2 percent of the 2,428 reaction pairs tested. An R-value of 0.93 between the two methods indicates that the monoclonal antibody mixture method of the present invention did not affect the microcytotoxicity test. Furthermore, the viability of the lymphocytes was unaffected. Any discrepancies are believed due to primarily serological problems such as weak antisera and weak contaminating or cross-reacting antibodies.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein and is defined only by the following claims.

What is claimed is:

1. A composition of matter adapted for use in separating a given amount of a subpopulation of cells bearing a specific immunogenic marker from a heterogeneous cell suspension, said composition of matter consisting essentially of an aqueous solution of:
   a sufficient amount of a monoclonal antibody which recognizes a specific immunogenic marker and is immunoreactive with a subpopulation of cells to form an antibody tagged subpopulation of cells, said subpopulation of cells being present within a heterogeneous cell suspension;
   complement in an amount sufficient to provide lysing of substantially all of said antibody tagged subpopulation cells to provide lysed subpopulation cells having a density less than the density of the nonlysed cells in said heterogeneous cell suspension; and
   a sufficient amount of a density gradient media consisting essentially of colloidal silica or cesium chloride to provide a solution after addition of said heterogeneous cell suspension having a density greater than said lysed subpopulation cells, but less than the density of the nonlysed cells in said heterogeneous cell suspension, said density gradient media being nontoxic with respect to the cells in said heterogeneous cell suspension.

2. A composition of matter according to claim 1 wherein said heterogeneous cell population includes lymphocytes, granulocytes, red blood cells and monocytes, said composition of matter adapted for use in separating red blood cells, granulocytes and monocytes from lymphocytes in said heterogeneous cell suspension wherein said composition includes monoclonal antibodies which recognize and are immunoreactive with specific immunogenic markers on said red blood cells, granulocytes and monocytes to form an antibody tagged subpopulation of red blood cells, granulocytes and monocytes which are susceptible to lysing by said complement, said composition of matter being useful in removing said red blood cells, granulocytes and monocytes from said heterogeneous cell suspension to isolate said lymphocytes.

3. A composition of matter according to claim 2 wherein said heterogeneous cell population includes B lymphocytes and T lymphocytes, said specific antibody further including monoclonal antibodies which recognize B lymphocytes, said composition of matter being useful in removing said red blood cells, granulocytes, monocytes and B lymphocytes from said heterogeneous cell suspension to isolate T lymphocytes.

4. A composition of matter according to claim 3 wherein said heterogeneous cell population includes helper T lymphocytes and suppressor T lymphocytes, said specific antibody further including monoclonal antibodies which recognize helper T lymphocytes, said composition of matter being useful in removing said red blood cells, granulocytes, monocytes and B lymphocytes and helper T lymphocytes from said heterogeneous cell suspension to isolate said suppressor T lymphocytes.

5. A composition of matter according to claim 3 wherein said heterogeneous cell population includes helper T lymphocytes and suppressor T lymphocytes, said specific antibody further including monoclonal antibodies which recognize suppressor T lymphocytes, said composition of matter being useful in removing said red blood cells, granulocytes, monocytes and B lymphocytes and suppressor T lymphocytes from said heterogeneous cell suspension to isolate said helper T lymphocytes.

6. A composition of matter according to claim 2 wherein said heterogeneous cell population includes B lymphocytes and T lymphocytes, said specific antibody further including monoclonal antibodies which recognize T lymphocytes, said composition of matter being useful in removing said red blood cells, granulocytes, monocytes and T lymphocytes from said heterogeneous cell suspension to isolate said B lymphocytes.

7. A composition of matter according to claim 1 wherein said heterogeneous cell suspension includes lymphocytes, granulocytes, red blood cells and monocytes, wherein said composition includes one or more monoclonal antibodies which recognize and are immunoreactive with red blood cells, granulocytes and lymphocytes, said composition of matter being useful in removing said red blood cells, lymphocytes and granulocytes from said heterogeneous cell suspension to isolate said monocytes.

8. A composition of matter according to claim 1 wherein said heterogeneous cell suspension includes lymphocytes, granulocytes, red blood cells and monocytes, wherein said composition includes one or more monoclonal antibodies which recognize and are immunoreactive with red blood cells, lymphocytes and monocytes, said composition of matter being useful in removing said red blood cells, lymphocytes and monocytes from said heterogeneous cell suspension to isolate said granulocytes.

9. A composition of matter according to claim 1 wherein said heterogeneous cell suspension includes lymphocytes, granulocytes, red blood cells and monocytes, wherein said lymphocytes include B lymphocytes, T lymphocytes and null lymphocytes, said composition including one or more monoclonal antibodies which recognize and are immunoreactive with red blood cells, monocytes, granulocytes, T lymphocytes and B lymphocytes, said composition of matter being useful in isolating said null lymphocytes from said heterogeneous cell suspension.

10. A composition of matter according to claim 1 wherein said heterogeneous cell suspension includes lymphocytes, granulocytes, red blood cells and monocytes, wherein said granulocytes include basophils, eosinophils and neutrophils said composition including one or more monoclonal antibodies which recognize and are immunoreactive with monocytes, lymphocytes, red blood cells, neutrophils and basophils, said composition of matter being useful in isolating eosinophils from said heterogeneous cell suspension.

11. A composition of matter according to claim 1 wherein said heterogeneous cell suspension includes lymphocytes, granulocytes, red blood cells and monocytes, wherein said granulocytes include basophils, eosinophils and neutrophils, said composition including one or more monoclonal antibodies which recognize and are immunoreactive with monocytes, lymphocytes, red blood cells, basophils and easinophils, said composition of matter being useful in isolating neutrophils from said heterogeneous cell suspension.

12. A composition of matter according to claim 1 wherein said heterogeneous cell suspension includes lymphocytes, granulocytes, red blood cells and monocytes, wherein said granulocytes include basophils, eosinophils and neutrophils, said composition including one or more monoclonal antibodies which recognize and are immunoreactive with monocytes, lymphocytes, red blood cells, eosinophils and neutrophils, said composition of matter being useful in isolating basophils from said heterogeneous cell suspension.

13. A composition of matter according to claim 1 wherein said density gradient media comprises colloidal silica particles coated with a non-toxic polymer.

14. A composition of matter according to claim 13 wherein said polymer coating consists essentially of polyvinylpyrolidone.

15. A composition according to claim 13 wherein said colloidal silica particles are different sizes.

16. A composition according to claim 1 wherein said complement is rabbit complement.

17. A composition according to claim 1 wherein said solution comprises from 40 to 60 volume percent density gradient media.

18. A composition of matter according to claim 1 adapted for use in removing red blood cells and granulocytes bearing specific immunogenic markers from a heterogeneous cell population including lymphocytes, granulocytes, red blood cells and monocytes, said composition further including:
   a sufficient amount of a monoclonal antibody which recognizes and is immunoreactive with an immunogenic marker on said red blood cell to form an antibody tagged subpopulation of red blood cells which are susceptible to lysing by said complement; and
   a sufficient amount of a monoclonal antibody which recognizes and is immunoreactive with said immunogenic marker on said granulocyte to form an antibody tagged subpopulation of granulocytes which are susceptible to lysing by said complement.

* * * * *